United States Patent [19]

Naumann et al.

[11] 4,345,090
[45] Aug. 17, 1982

[54] PROCESS FOR PREPARING MENTHYL ESTERS OF ENANTIOMERS OF CHIRAL 3-(2,2-DICHLORO- AND -DIBROMO-VINYL)-2,2-DIMETHYLCYCLO-PROPANECARBOXYLIC ACIDS

[75] Inventors: Klaus Naumann, Cologne; Rudolf Rauchschwalbe, Wuppertal, both of Fed. Rep. of Germany

[73] Assignee: Bayer Aktiengesellschaft, Leverkusen, Fed. Rep. of Germany

[21] Appl. No.: 163,361

[22] Filed: Jun. 26, 1980

[30] Foreign Application Priority Data

Jul. 13, 1979 [DE] Fed. Rep. of Germany ....... 2928406

[51] Int. Cl.$^3$ ..................... C07C 67/52; C07C 69/743
[52] U.S. Cl. .................................... 560/124; 560/219; 562/401; 204/163 R
[58] Field of Search ................. 560/124; 562/506, 401

[56] References Cited

U.S. PATENT DOCUMENTS 4,024,163  5/1977  Elliott ................................ 560/124

FOREIGN PATENT DOCUMENTS 42-10220  6/1967  Japan .................................... 560/124
54-73758  6/1979  Japan .

OTHER PUBLICATIONS

Eliel, "Stereochemistry of Carbon Compounds," pp. 49–52.
Elliott, J. Agric. Food Chem. 24, pp. 270–276 (1976).

Primary Examiner—Michael L. Shippen
Attorney, Agent, or Firm—Sprung, Horn, Kramer & Woods

[57]        ABSTRACT

A substantially pure compound selected from the group consisting of the d-menthyl esters of 1RS-cis-, 1RS-cis/trans-, 1R-cis-, 1S-cis-, 1R-trans- and 1S-trans-3-(2,2-dichloro- and dibromo-vinyl)-2,2-dimethylcyclopropanecarboxylic acid, the l-menthyl esters of 1RS-cis-, 1RS-trans-, 1RS-cis/trans-, 1R-cis-, 1S-cis-, 1R-trans- and 1S-trans-3-(2,2-dibromo-vinyl)-2,2-dimethylcyclopropanecarboxylic acid and the l-menthyl esters of 1R-trans- and 1S-trans-3-(2,2-dichloro-vinyl)-2,2-dimethyl-cyclopropanecarboxylic acid. The esters are produced by reacting enantiomers of the acids with d- or l-menthol are selectively crystallizing.

5 Claims, No Drawings

PROCESS FOR PREPARING MENTHYL ESTERS OF ENANTIOMERS OF CHIRAL 3-(2,2-DICHLORO- AND -DIBROMO-VINYL)-2,2-DIMETHYLCYCLO-PROPANECARBOXYLIC ACIDS

The present invention relates to certain new menthyl esters of substituted cyclopropanecarboxylic acids, to a process for their preparation and to their use for separating the enantiomers of these carboxylic acids.

The l-menthyl esters of 1 RS-cis-, 1 RS-trans, 1 R-cis- and 1 S-cis-3-(2,2-chlorovinyl)-2,2-dimethyl-cyclopropanecarboxylic acid (permethric acid) are known from J. Agric. Food. Chem. volume 24, No. 2, 1976, pages 270 et seq. The compounds are prepared by reacting l-menthol with the corresponding isomer or isomer mixture of the acid chloride. The compounds were prepared to investigate the cis/trans-epimerization of permethric acid. There are no statements regarding an industrial use of these compounds. Moreover, no statements have been made regarding the preparation and use of the remaining menthyl ester isomers of permethric acid. R and S characterize absolute configurations of the denoted C-atoms. R characterizes the (+) enantiomeres, RS characterizes the razemates.

The present invention now provides:

(1), as new compounds, the d-menthyl esters of 1 RS-cis-, 1 RS-trans-, 1RS-cis/trans-, 1R-cis/trans, 1S-cis/trans, 1R-cis-, 1S-cis-, 1R-trans- and 1S-trans-3-(2,2-dichloro- and dibromo-vinyl)-2,2-dimethyl-cyclopropanecarboxylic acid, the l-menthyl esters of 1RS-cis-, 1RS-trans-, 1RS-cis/trans-, 1R cis/trans, 1S cis/trans, 1R-cis-, 1S-cis-, 1R-trans- and 1S-trans-3-(2,2-dibromo-vinyl)- 2,2-dimethyl-cyclopropanecarboxylic acid and the l-menthyl esters of 1R-trans- and 1S-trans-3-(2,2-dichlorovinyl)-2,2-dimethyl-cyclopropanecarboxylic acid;

(2) a process for the preparation of a diastereomer or diastereomer mixture selected from the 3-(2,2-dichloro and -dibromo-vinyl)-2,2-dimethyl-cyclopropanecarboxylic acid d- and l-menthyl esters according to 1 (above), characterized in that
(a) the corresponding acid or a reactive derivative thereof is reacted with d- or l-menthol, or
(b) a menthyl ester of the general formula

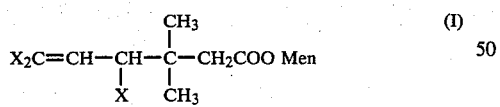

in which X represents chlorine or bromine and Men represents the l- or d-menthyl radical, is subjected to cyclizing dehydrohalogenation, or
(c) a menthyl ester of the general formula

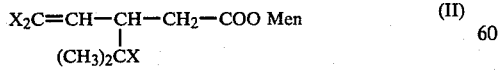

in which X and Men have the meaning indicated above, is subjected to cyclizing dehydrohalogenation, or
(d) diazoacetic acid d- or l-menthyl ester is reacted with 1,1-dichloro- or dibromo-4-methyl-penta-1,3-diene in the presence of a copper compound, or (e) in the case where the d-menthyl ester of a 1R-cis-acid is desired, a mixture of the corresponding 1 RS-cis-acids or of reactive derivatives thereof is reacted with d-menthol and the more sparingly soluble d-menthyl ester of the 1R-cis-acid is separated off from an organic diluent in the customary manner, or (f) in the case where the l-menthyl ester of a 1S-cis-acid is desired, a mixture of the corresponding 1 RS-cis-acids or of reactive derivatives thereof is reacted with l-menthol and the more sparingly soluble l-menthyl ester of the 1S-cis-acid is separated off from an organic diluent in the customary manner (this variant also being suitable for the preparation of the known 1S-cis-l-menthyl ester of the permethric acid), or (g) in the case where the d-menthyl ester of a 1R-trans-acid is desired, a mixture of the corresponding 1 RS-trans-acids or a mixture of the corresponding 1 RS-cis/trans-acids or of reactive derivatives thereof is reacted with d-menthol, or the reaction according to (b), (c) or (d) above is carried out with the corresponding d-menthyl esters, and the more sparingly soluble 1R-trans-d-menthyl ester is separated off from an organic diluent in the customary manner, or (h) in the case where the l-menthyl ester of a 1S-trans-acid is desired, a mixture of the corresponding 1RS-trans-acids or a mixture of the corresponding 1RS-cis/trans-acids or of reactive derivatives thereof is reacted with l-menthol, or the reaction according to (b), (c) or (d) above is carried out with the corresponding l-menthyl esters, and the more sparingly soluble l-menthyl ester of the 1S-trans-acid is separated off from an organic diluent in the customary manner;

(i) in the case where the mixture of the d-menthyl esters of 1R cis/trans-acid is desired, a mixture of the corresponding 1 RS-cis/trans-acids or of reactive derivatives thereof is reacted with d-menthol, or the reaction according to (b), (c) or (d) above is carried out with the corresponding d-menthyl esters, and the in ligroin more sparingly soluble, 1R cis/trans-d-menthyl ester is separated off from ligroin in the customary manner, or (k) in the case where the mixture of the l-menthyl esters of 1 S cis/trans-acid is desired, a mixture of the corresponding 1RS-cis/trans-acids or of reactive derivatives thereof is reacted with l-menthol, or the reaction according to (b), (c) or (d) above is carried out with the corresponding l-menthyl esters, and the inligroin more sparingly soluble l-menthyl ester of the 1S cis/trans-acid is separated off from ligroin in the customary manner;

(3) a process for separating off 1R-cis-3-(2,2-dichloro- or dibromo-vinyl)-2,2-dimethyl-cyclopropanecarboxylic acid from a mixture of the corresponding 1RS-cis-acids, characterized in that the mixture of these acids or of their reactive derivatives is reacted with d-menthol, the 1R-cis-acid d-menthyl ester, which is more sparingly soluble in organic diluents, is separated off and the 1R-cis-acid is liberated by saponifying the ester;

(4) a process for separating off 1S-cis-3-(2,2-dichloro- or dibromovinyl)-2,2-dimethyl-cyclopropanecarboxylic acid from a mixture of the corresponding 1RS-cis-acids, characterized in that the mixture of these acids or of reactive derivatives thereof is reacted with l- menthol, the 1S-cis-acid l-menthyl ester, which is more sparingly soluble in organic diluents, is separated off and the 1S-cis-acid is liberated by saponifying the ester;

(5) a process for separating off 1R-trans-3-(2,2-dichloro- or dibromovinyl)-2,2-dimethyl-cyclopropanecarboxylic acid from a mixture of the corresponding 1RS-trans-acids or a mixture of the corresponding 1RS-cis/trans-acids, characterized in that the mixture of these acids or of reactive derivatives thereof is reacted with d-menthol, or the reaction according to 2(b), (c) or (d) above is carried out with the corresponding d-menthyl esters, the 1R-trans-acid d-menthyl ester, which is more sparingly soluble in organic diluents, is separated off and the 1R-trans-acid is liberated by saponifying the ester; and (6) a process for separating off the mixture of 1R-cis/-trans 3-(2,2-dichloro or dibromo-vinyl)-2,2-dimethyl-cyclopropanecarboxylic acid from a mixture of the corresponding 1RS cis/trans-acids, characterized in that the mixture of these acids or of their reactive derivatives is reacted with d-menthol, the 1R cis/-trans acid d-menthyl ester, which is more sparingly soluble in ligroin, is separated off and the 1R-cis/-trans-acid is liberated by saponifying the ester;

(7) a process for separating off 1S-trans-3-(2,2-dichloro or dibromovinyl)-2,2-dimethyl-cyclopropanecarboxylic acid from a mixture of the corresponding 1RS-trans-acids or a mixture of the corresponding 1RS-cis/trans-acids, characterized in that the mixture of these acids or of reactive derivatives thereof is reacted with l-menthol, or the reaction according to 2(b), (c) or (d) above is carried out with the corresponding d-menthyl esters, the 1S-trans-acid l-menthyl ester, which is more sparingly soluble in organic diluents, is separated off and from the more soluble esters the scarcely 1S-trans-containing mixture of the acids is liberated by saponifying the esters.

The new menthyl esters can thus be employed in an industrially simple manner for separating the enantiomers of 3-(2,2-dichloro- or dibromovinyl)-2,2 dimethyl-cyclopropanecarboxylic acids. This was astonishing since 3-(2-methyl-propen-1-yl)-2,2-dimethyl-cyclopropanecarboxylic acid cannot be split into the enantiomers via their corresponding menthyl esters.

The separation of the enantiomers of these acids was hitherto carried out by fractional precipitation or crystallization of the diastereomeric salts of the free acids with optionally active amines (see, for example, Derwent Basical Abstr. Journal 45194 W/27, 21671 W/13, 13445 W/08; DE-OS (German Published Specification) 2,549,177; and French Patent 1,536,468). These processes are troublesome when applied on a large scale, since they require, for example, many crystallization stages and usually give the desired enantiomer in unsatisfactory yield. In addition, optically active amines are required and these are not readily available in relatively large amounts.

The separation of the enantiomers of these acids with the aid of the menthyl esters has a number of advantages: thus, the process leads to optically pure compounds in high yield in only a few crystallization steps. Another advantage is the use of inexpensive, optically pure l- or d-menthol, which can easily be recovered. The preparation of optically pure 1R-cis-permethric acid, which could hitherto be achieved only with difficulty, also readily leads to relatively large amounts by the process according to the invention. A particular advantage is the possibility of selectively separating off the d- or l-menthyl esters of the 1R-trans- or 1S-trans permethric acid from the mixture with the corresponding esters in the cis-configuration, and the separation of a mixture of 1S-cis/trans-menthylesters or 1 R cis/trans d-menthylesters from the mixture of the racemic 1RS-cis/trans esters with l- or d-menthol.

Separation of the enantiomers with the aid of the menthyl esters is especially suitable for rapidly obtaining relatively large amounts of pure enantiomers. The desired acids can be liberated from the esters by alkaline saponification.

The new menthyl esters according to 1 (above) are prepared by methods which are in themselves known. Thus, process 2(a) above is carried out analogously to the customary esterification methods, such as reaction of d- or l-menthol (a) with the free acids in the presence of a water-binding agent, (b) with the acid chlorides in the presence or absence of an acid-trapping agent or solvent or (c) with the lower alkyl esters of the acids in the presence of a trans-esterification catalyst, such as titanium tetramethanolate (ananlogously to the method in Dutch Pat. No. 7,805,738).

Process 2(b) is carried out analogously to the process described in DE-OS (German Published Specification) No. 2,539,895. Process 2(c) is carried out analogously to the process described in DE-OS (German Published Specification) No. 2,723,447. Process 2(d) is carried out analogously to the process described in DE-OS (German Published Specification) No. 2,634,663.

The starting compounds used in processes 2(a)–(h) are known, or, in the case of compounds of the formula (I) or (II), can be prepared by known processes. l-Menthol is 1R,3R,4S-p-menthan-3-ol and d-menthol is 1S,3S,4R-p-menthan-3-ol.

If, for example, 1mole of racemic cis-permethric acid chloride and 1 mole of d-menthol are used as the starting compounds in process 2(e), a mixture of the diastereomeric d-menthyl esters can be obtained by simple warming:

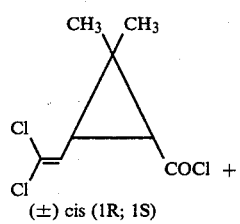

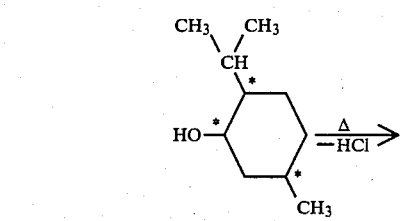

-continued

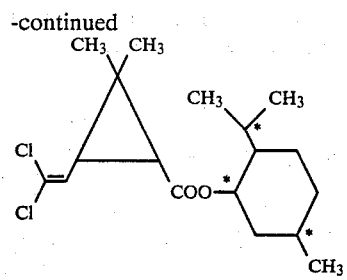

After dissolving the mixture in twice the amount of petroleum ether and cooling the solution to −10° C., 1R-cis-permethric acid d-menthyl ester crystallizes out, and, after one or two crystallizations from petroleum ether is optically pure. Alkaline saponification in methanol at 120° C. in an autoclave for 5 hours gives 1R-cis-permethric acid in a total yield of 70%; $[\alpha]_{20}^D$: +27.7° (C=1, CHCl₃) (Literature: DOS (German Published Specification) 2,549,177, $[\alpha]_{20}^D$: +27.2°).

The mixture of the diastereomeric menthyl esters obtained by processes 2(e)–(k) is dissolved in the same amount, or several times, preferably twice, the amount, of an organic diluent. Possible diluents are non-polar diluents, such as alkanes with up to 10 C atoms, for example petroleum ether, ligroin or wash benzine, or strongly polar diluents such as alcohols, and, if appropriate, even aqueous alcohols or ketones, e.g. containing up to 8 carbon atoms.

The more sparingly soluble enantiomers are separated off at temperatures from +30° to −80° C., preferably from +20° to −30° C. One diastereomer thereby crystallizes out, and is filtered off at the crystallization temperature and recrystallized once or several times from the same solvent in order to obtain complete optical purity.

The enantiomeric carboxylic acids are then liberated in the form of their alkali metal salts by alkaline saponification of the menthyl esters with alkali metal hydroxides in organic solvents such as alcohols. To accelerate the reaction, this saponification can be carried out at elevated temperatures in relatively high-boiling solvents, for example glycol or di-phenyl ether, but also in low-boiling solvents, such as methanol, under pressure. The unchanged menthol, which can be recovered completely, is suitable for further reactions, as described.

In a particular embodiment of the process according to 2(g), the ester of the 1R-trans-acid is selectively separated off as crystals, in high yields, from the mixture of the d-menthyl esters of cis- and trans-permethric acid containing the 4 diastereomers. A small amount of photosensitizer, for example cyclohexanone, is then added to the mother liquor and the mixture is irradiated with an ultraviolet light source, such as is described in principle in U.S. Pat. No. 3,657,086 and DE-OS (German Published Specification) No. 2,628,477, at temperatures between −70° C. and +100° C. until the optical rotation no longer changes. On cooling, the 1R-trans-ester again crystallizes out of the racemic cis/trans mixture isomerized in this way in the acid part of the ester. The mother liquor is then again subjected to photoisomerization.

Thus, finally, the entire d-menthyl ester mixture of the originally racemic cis/trans-acid can be converted into the 1R-trans-ester.

If the esters of naturally occurring l-menthol with racemic cis/trans-permethric acid are used, a permethric acid which contains only small residues of the 1S-trans-acid can be obtained by separating off the sparingly soluble ester of the 1S-trans-acid and then saponifying the readily soluble constituents of the mother liquor.

The pure optically active cyclopropanecarboxylic acids of the formula I, in the 1R-configuration or 1S-configuration, thus obtained are used for the preparation of highly active insecticides of the pyrethroid type.

The examples which follow illustrate the process according to the invention, without indicating a limitation with regard to the extent of its use.

The following menthyl esters, for example, were obtained by these examples (melting points are in °C. and boiling points are in °C./mm Hg).

A. 3-(2,2-Dichlorovinyl)-2,2-dimethylcyclopropanecarboxylic acid

| Ester | Physical properties |
|---|---|
| (±)-(1RS)-cis-acid d-menthyl ester mixture | Melting point: 96° C. |
| (±)-(1RS)-trans-acid d-menthyl ester mixture | Melting point: 101° C. |
| (±)-(1RS)-cis/trans-acid d-menthyl ester mixture | Boiling point: 130–140° C./0.1 |
| (±)-(1RS)-cis-acid d-menthyl ester | Melting point: 96° C. $[\alpha]_{13}^D = +73.6°$ |
| (−)-(1S)-cis-acid d-menthyl ester | Melting point: 57° C. |
| (+)-(1R)-trans-acid d-menthyl ester | Melting point: 104° C. $[\alpha]_{20}^D = +69.8°$ |
| (−)-(1S)-trans-acid d-menthyl ester | |
| (+)-(1S)-trans-acid l-menthyl ester | |
| (−)-(1S)-trans-acid l-menthyl ester | Melting point: 104° C.; $[\alpha]_{20}^D = -69.3°$ |

B. 3-(2,2-Dibromovinyl)-2,2-dimethylcyclopropanecarboxylic acid

| | |
|---|---|
| (±)-(1RS)-cis/trans-acid d-menthyl ester | |
| (±)-(1RS)-cis/trans-acid l-menthyl ester | |
| (±)-(1RS)-cis-acid d-menthyl ester | |
| (±)-(1RS)-cis-acid l-menthyl ester | |
| (±)-(1RS)-trans-acid d-menthyl ester | Boiling point: 160–170° C./0.1 |
| (±)-(1RS)-trans-acid l-menthyl ester | |
| (+)-(1R)-cis-acid d-menthyl ester | |
| (+)-(1R)-cis-acid l-menthyl ester | |
| (−)-(1S)-cis-acid d-menthyl ester | |
| (−)-(1S)-cis-acid l-menthyl ester | |
| (+)-(1R)-trans-acid d-menthyl ester | melting point: 107° C./ $[\alpha]_{20}^D = +42.1°$ (CHCl³) |
| (+)-(1R)-trans-acid l-menthyl ester | |
| (−)-(1S)-trans-acid d-menthyl ester | |
| (−)-(1S)-trans-acid l-menthyl ester | melting point: 107° C./ $[\alpha]_{20}^D = -42.1°$ CHCl³ |

EXAMPLE 1

1.0 mole of (+)-cis-3-(2,2-dichlorovinyl)-2,2-dimethylcyclopropanecarboxylic acid chloride was added dropwise to a mixture of 1.0 mole of d-menthol ($[\alpha]_{20}^D$: +47.9° (ethanol)) and 1.0 mole of triethylamine in 0.7 liter of petroleum ether. The mixture was then boiled until the acid chloride had been consumed, extracted by shaking with water and dilute H₂SO₄, dried and cooled to −10° C. After some time, the d-methyl ester of 1R-cis-acid crystallized out and was recrystallized once more with twice the amount of petroleum ether. Yield: 90%; melting point: 96° C.; $[\alpha]_{10}^D$: +73.6° (C=1, CHCl₃).

This ester was saponified with 1 mole of KOH in 1 liter of methanol at 120° C. in an autoclave for 6 hours. After distilling off the methanol over a column, the residue was extracted with water/petroleum ether. The d-menthol was recovered from the petroleum ether phase and the aqueous solution was acidified and extracted with petroleum ether. After stripping off the solvent, the (+)-cis-acid remained: $[\alpha]_{20}{}^D$: +27.7° (CHCl$_3$).

The acid chloride was prepared from this acid: boiling point: 68° C./0.01 mm Hg; $[\alpha]_{20}{}^D$: +17.0° (CHCl$_3$).

EXAMPLE 2

With the aid of l-menthol, the optically pure (−)-cis-acid was obtained analogously to Example 1. $[\alpha]_{20}{}^D$: −27.7° (CHCl$_3$).

EXAMPLE 3

The (+)-trans-acid, $[\alpha]_{20}{}^D$: +36° (CHCl$_3$), was obtained analogously to Example 1 from (+)-trans-3-(2,2-dichloromethyl)-2,2-dimethyl-cyclopropanecarboxylic acid chloride and d-menthol. Melting point of the d-menthyl ester of the (+)-trans-acid: 92° C.; $[\alpha]_{20}{}^D$: +69.5° (C=1, CHCl$_3$).

EXAMPLE 4

The mother liquor from Example 3 was saponified as described in Example 1 and, after recrystallizing the product once from petroleum ether and separating off the racemic sparingly soluble constituents, optically pure (−)-trans-acid was obtained. $[\alpha]_{20}{}^D$: −36.0° (CHCl$_3$). The NMR spectra of the acid were identical to those described.

EXAMPLE 5

The procedure followed was analogous to Example 1, using (±)-cis/trans-3-(2,2-dichlorovinyl)-2,2-dimethylcyclopropanecarboxylic and d-menthol. The diastereomer mixture was obtained: boiling point: 120°–130° C./0.1 mm Hg (yield: 95%). The d-menthyl ester of the (±)-trans-acid slowly crystallized out, in 84% yield, from twice the amount of petroleum ether at −20° C. According to a determination by capillary gas chormatography, the ester contained the menthyl ester of the 1R-trans-acid to the extent of 83%. The menthyl ester of the 1S-trans-acid to the extent of 7%, the menthyl ester of the 1R-cis-acid to the extent of 5.6% and the menthyl ester of the 1S-acid to the extent of 3.4%. After recrystallizing the product twice, the 1R-trans-ester content had increased to 94%.

Saponification with KOH in glycol at 120° C. gave, after 5 hours, the (+)-trans-acid. $[\alpha]_{20}{}^D$: +34°.

EXAMPLE 6

0.5 mol of (±)-cis/trans-3-(2,2-dichlorovinyl-2,2-dimethylcyclopropanecarboxylic acid chloride was added dropwise to 0.7 mole of l-menthol at 100° C. The HCl gas immediately evolved was removed with a gentle stream of nitrogen. After distillation, a mixture of the diastereomeric l-menthyl esters was obtained in 95% yield. Boiling point: 120°–150° C./0.1 mm Hg. After crystallization as described, an ester with a greatly reduced content of 1S-trans-ester was obtained from the mother liquor and was saponified as in Example 1.

EXAMPLE 7

5 g of titanium tetraethylate were added to 1 mole of a 40/60 mixture of (±)-cis/trans-3-(2,2-dichlorovinyl)-2,2-dimethylcyclopropanecarboxylic acid ethyl ester and 1.5 moles of d-menthol in 40 ml of methanol. On heating the suspension, methanol was distilled off. The residual mixture was now heated to 150° C. for 6 hours. 20 ml of absolute toluene were then added slowly, and a further 300 ml of toluene were then added dropwise at an internal temperature of 150° C., the toluene being distilled off at the same rate. The mixture was then distilled under 0.1 mm Hg, unreacted ethyl ester and menthol first being separated off. In relation to the 56% conversion, the menthyl esters were obtained almost quantitatively. Boiling point: 120°–150° C./mm Hg. The 1R-trans-ester crystallized out, in 85% yield, from a solution of the product in twice the amount of petroleum ether at −5° C.

EXAMPLE 8

After separating off the crystalline ester from the mother liquor obtained in Example 7, 15 g of cyclohexanone were added to the liquor and the mixture was irradiated with a high pressure mercury lamp at 40° C. under an inert nitrogen atmosphere. After 6 hours, the mixture was cooled again to −15° C. in order subsequently to filter off further 1R-trans-ester, which was recrystallized from petroleum ether at −5° C. together with the crystals from Example 7. The mother liquors were combined and subjected to renewed photoisomerization.

EXAMPLE 9

1RS-trans-3-(2,2-Dibromovinyl)-2,2-dimethylcyclopropanecarboxylic acid chloride was esterified with l-menthol analogously to Example 1. Boiling point of the ester: 160° C./0.1 mm Hg. Yield: 73%. On cooling the petroleum ether solution to −50° C., the ester of the 1R-trans-acid slowly crystallized out. Melting point: 107° C.; $[\alpha]_{20}{}^D$: −42.1° (C=1, CHCl$_3$).

NMR spectrum (CHCl$_3$): d 6.2 ppm (1) and m 4.4–5.0 ppm (1) to 0.7–2.3 ppm (26).

EXAMPLE 10

α-Isopropyl-p-chlorophenylacetic acid chloride was reacted with l-menthol analogously to Example 1 to give the l-menthyl ester, boiling point: 180°–190° C./0.1 mm Hg. It was not possible to separate off one diastereomer by the method described in the preceding examples.

EXAMPLE 11

Chrysanthemoyl chloride (cis/trans) were esterified with l-menthol analogously to Example 5; boiling point: 130°–140° C./0.1 mm Hg. It was not possible to separate off, from various solvents, one diastereomer of the product.

EXAMPLE 12

10 g of moist dibenzoyl peroxide were added to 1 mole of 3,3-dimethylpentenic acid in 1 liter of CCl$_4$. The water was then distilled out of the mixture and the residue was boiled for a further 5 hours. Still more dibenzoyl peroxide was added at intervals. On concentrating the mixture, 6,6,6,4-tetrachloro-3,3-dimethylhexanoic acid precipitated quantitatively. Melting point: 118° C.

IR spectrum (cm$^{-1}$), KBr tablet: 2300–3500, 1700, 1462, 1415, 1405, 1390, 1370, 1340, 1350, 1265, 1235, 1220, 1170, 1120, 1065, 1035, 990, 965, 945, 910, 820, 755, 750 and 680.

With regard to the acid part, the NMR spectrum corresponds to the values given for the ethyl ester in DE-OS (German Published Specification) No. 2,549,895, page 14.

0.1 mole of this acid was converted into the acid chloride in the customary manner, using $SOCl_2$ and a little dimethylformamide, and the acid chloride was esterified with d-menthol as described in Example 1; IR spectrum of the ester (film) $(cm^{-1})$; 2990, 1722, 1450, 1410, 1380, 1360, 1340, 1290, 1260, 1222-1190, 1130, 1110, 1666, 1630, 1010, 980, 960, 910, 890, 840, 810, 770, 750, 730, 710 and 680.

This ester was added to a solution of 0.2 mole of sodium d-menthylate (prepared from 0.2 mole of d-menthol and 0.2 mole of NaH) in absolute tetrahydrofuran. The mixture was stirred at room temperature until it gave a neutral reaction. After filtering the mixture, concentrating the filtrate and distilling the residue, permethric acid d-menthyl ester was obtained. Analysis by capillary gas chromatography gave the following proportions in the product: 36.9% of the 1R-trans-ester, 32.9% of the 1S-trans-ester, 16.4% of the 1R-cis-ester and 13.8% of the 1S-cis-ester.

A higher content of the 1R-trans-isomers was thus obtained by asymmetric induction.

The mixture was made to crystallize with petroleum ether as described in Example 5 and the mother liquor was subjected to photoisomerization as in Example 8.

EXAMPLE 13

The mixture of d-menthylesters of racemic cis trans (40/60) acid obtained in example 7 was dissolved in ligroin. When cooling to 10° C.–0° C. a mixture of d-menthyl-esters is crystallizing which contains 40% 1R cis- and 60% 1R trans esters.

It will be appreciated that the instant specification and examples are set forth by way of illustration and not limitation, and that various modifications and changes may be made without departing from the spirit and scope of the present invention.

We claim:

1. A process for obtaining a substantially pure compound selected from the group consisting of the d-menthyl esters of 1R-cis/trans, 1S-cis/trans, 1R-cis-, 1S-cis-, 1R-trans- and 1S-trans-3-(2,2-dichloro- and -dibromo-vinyl)-2,2-dimethylcyclo-propanecarboxylic acid, the l-menthyl esters of 1R-cis/trans-, 1R-cis, 1S-cis-, 1R-trans-, 1R-cis/trans, 1S-cis/trans, and 1S-trans-3-(2,2-dibromo-vinyl)-2,2-dimethyl-cyclo-propanecarboxylic acid and the l-menthyl esters of 1R-trans-, 1R-cis/trans, 1S-cis/trans, and 1S-trans-3-(2,2-dichloro-vinyl)-2,2-dimethyl-cyclopropane-carboxylic carboxylic acid, comprising reacting d-menthol or l-menthol with a mixture of 1 RS-cis-, 1RS-trans or a mixture of 1RS-cis- and 1RS-trans-3-(2,2-dichloro- or -dibro-movinyl)-2,2-dimethylcyclopropanecarboxylic acids or acid chlorides of such acids in a solvent selected from the group consisting of an alkane with up to 10 carbon atoms, and an alcohol and a ketone containing up to 8 carbon atoms to form a solution of the menthyl esters, and cooling the solution and/or removing some of the solvent preferentially to crystallize out one or more esters while leaving the solution preferentially enriched in one or more esters.

2. A process according to claim 1, comprising reacting d-menthol with a mixture of the 1RS-cis-3-(2,2-dichloro- or -dibromo-vinyl)-2,2-dimethylcyclopropanecarboxylic acids or acid chlorides thereof in a solvent selected from the group consisting of an alkane with up to 10 carbon atoms, and an alcohol and a ketone containing up to 8 carbon atoms to form a solution of d-menthyl 1RS-cis esters, and cooling the solution and/or removing some of the solvent preferentially to crystallize out one of the 1R and 1S-cis-esters while leaving the solution preferentially enriched in the other cis-ester.

3. A process according to claim 1, comprising reacting l-menthol with a mixture of the 1RS-cis-3-(2,2-dichloro- or -dibromo-vinyl)-2,2-dimethylcyclopropanecarboxylic acids or acid chlorides thereof in a solvent selected from the group consisting of an alkane with up to 10 carbon atoms, and an alcohol and a ketone containing up to 8 carbon atoms to form a solution of l-menthyl 1RS-cis esters, and cooling the solution and/or removing some of the solvent preferentially to crystallize out one of the 1R and 1S-cis-esters while leaving the solution preferentially enriched in the other trans-ester.

4. A process according to claim 1, comprising reacting d-menthol with a mixture of the 1RS-trans-3-(2,2-dichloro- or -dibromo-vinyl)-2,2-dimethylcyclopropanecarboxylic acids or acid chlorides thereof in a solvent selected from the group consisting of an alkane with up to 10 carbon atoms, and an alcohol and a ketone containing up to 8 carbon atoms to form a solution of d-menthyl 1RS-trans esters, and cooling the solution and/or removing some of the solvents preferentially to crystallize out one of the 1R and 1S-trans-esters while leaving the solution preferentially enriched in the other trans-ester.

5. A process according to claim 1, comprising reacting l-menthol with a mixture of the 1RS-trans-3-(2,2-dichloro- or -dibromo-vinyl)-2,2-dimethylcyclopropanecarboxylic acids or acid chlorides thereof in a solvent selected from the group consisting of an alkane with up to 10 carbon atoms, and an alcohol and a ketone containing up to 8 carbon atoms to form a solution of l-menthyl 1RS-trans ester, and cooling the solution and/or removing some of the solvent preferentially to crystallize out one of the 1R and 1S-trans-esters while leaving the solution preferentially enriched in the other trans-ester.

* * * * *